(12) United States Patent
Han

(10) Patent No.: US 9,192,619 B2
(45) Date of Patent: Nov. 24, 2015

(54) METHODS FOR ADMINISTRATION OF CITICOLINE IN STROKE TREATMENT

(71) Applicant: Peking University Third Hospital, Beijing (CN)

(72) Inventor: Hongbin Han, Beijing (CN)

(73) Assignee: PEKING UNIVERSITY THIRD HOSPITAL, Beijing (CN)

( * ) Notice: Subject to any disclaimer, the term of this patent is extended or adjusted under 35 U.S.C. 154(b) by 174 days.

(21) Appl. No.: 13/923,512

(22) Filed: Jun. 21, 2013

(65) Prior Publication Data
US 2013/0288995 A1 Oct. 31, 2013

Related U.S. Application Data

(63) Continuation of application No. PCT/CN2010/080202, filed on Dec. 23, 2010.

(51) Int. Cl.
*A61K 31/7068* (2006.01)
*A61K 9/00* (2006.01)

(52) U.S. Cl.
CPC ............... *A61K 31/7068* (2013.01); *A61K 9/00* (2013.01)

(58) Field of Classification Search
CPC .................................................. A61K 31/7068
See application file for complete search history.

(56) References Cited

U.S. PATENT DOCUMENTS

| 6,123,956 A * | 9/2000 | Baker et al. ................... 424/426 |
| 2012/0238865 A1 | 9/2012 | Han |
| 2012/0239000 A1 | 9/2012 | Han |

FOREIGN PATENT DOCUMENTS

| CN | 1803126 | 7/2006 |
| CN | 102293634 A | 12/2011 |
| EP | 1 921 147 A2 | 5/2008 |
| WO | WO 94/02618 A1 | 2/1994 |
| WO | WO 95/23221 A1 | 8/1995 |
| WO | WO 2012/080202 A1 | 6/2012 |

OTHER PUBLICATIONS

Han et al., Sci. China Life Sci., 2011, 54, p. 235-239, published online Feb. 19, 2011.*
Savci et al., Naunyn-Schmiedeberg's Arch. Pharmacol., 2002, 365, p. 388-398.*
Certified copy of the PCT/CN2010/080202 priority application, published Jun. 28, 2012, retreived from WIPO.*
PCT International Search Report, Jan. 13, 2012 for PCT/EP/2011/072511.
International Preliminary Report on Patentability for International Patent Application No. PCT/CN2010/080202 mailed on Jun. 25, 2013.
Jeffrey Iliff, Hedok Lee; Mei Yu; Tian Feng, Jean Logan, Maiken Nedergaard, and Helene Benveniste, "Brain-Wide Pathway for Waste Clearance Captured by Contrast-Enhanced MRI",The Journal of Clinical Investigation, vol. 123,No. 3, Mar. 2013.

* cited by examiner

*Primary Examiner* — Jonathan S Lau
(74) *Attorney, Agent, or Firm* — Frommer Lawrence & Haug LLP; William S. Frommer

(57) ABSTRACT

The present invention provides administration methods for CDPC for treating stroke. CDPC was delivered via ECS at a concentration of 40 mmol/L-60 mmol/L. In a specific embodiment of the present invention, the concentration of CDPC administered is 50 mmol/L, CDPC is delivered at one time, the flow rate of administration is 0.2 μL/min, the volume of CDPC is 1.33 μL/mL of brain tissue, and the CDPC is administered in the caudate nucleus. The method can decrease the concentration of CDPC entering the brain and further decrease the dosage while improving efficacy. Thus, the result is improved and the probability of adverse effects due to the drug is reduced.

16 Claims, 5 Drawing Sheets

METHODS FOR ADMINISTRATION OF CITICOLINE IN STROKE TREATMENT

FIELD OF THE INVENTION

The present invention relates to administration methods. In particular, it relates to methods for the administration of citicoline (CDPC) for treating stroke.

BACKGROUND OF THE INVENTION

Cerebrovascular disease is a group of brain dysfunctions related to disease of the blood vessels supplying the brain. A stroke, or cerebrovascular accident (CVA), is an acute cerebral circulation disorder, which can quickly lead to localized or diffused brain impairment in clinical events. Existing drugs for treating acute cerebral ischemic stroke can be divided into two categories: drugs that improve cerebral blood flow and neuroprotective drugs.

The delivery effectiveness is critical in the treatment of acute ischemic stroke. Neuroprotective drugs have various species. Over the past two decades, many investigators in different countries have spent billions of dollars on the development of neuroprotective drug species according to the mechanism of neuronal damage after cerebral ischemia at a cellular or molecular level. Since the 1950's, CDPC has been researched as a neuroprotective drug. The Takeda pharmaceutical company from Japan first successfully developed Nicholin (citicoline) to cure the disturbance of consciousness. In 2002, Davalos et al. analyzed the effect of oral CDPC treatment of ischemic stroke by evidence based on clinical trials. In 2005, Hurtado and others made a model of focal brain ischemia using adult male Fischer rats, then injected CDPC into the abdominal cavity of the Fischer rats and blocked the middle cerebral artery one hour after the injection. Hurtado's results demonstrate that injecting CDPC with different dosages (e.g., 0.5 g/kg, 1 g/kg and 2 g/kg) can reduce infarct size of the neostriatum. According to the study of Hurtado in 2008, comparing to the control group, 48 hour-brain infarct size can be reduced significantly if 2 g/kg of CDPC are injected into the abdominal cavity of Fischer rats four hours after embolism caused by focal brain ischemia. Clinical research and animal experiments have confirmed that CDPC has a significant neuroprotective function. Mechanistic studies also show that CDPC plays a role in protecting the brain from ischemia and treating injury mainly through stabilizing the cell membrane, suppressing the release of free fatty acid, reducing free radical generation and inhibiting cell apoptosis. The United States is currently conducting Phase III clinical trials for the treatment of stroke by oral administration of CDPC, but the treatment effect is not satisfactory.

It is generally believed that the unsatisfactory result is associated with the blood-brain barrier (BBB) of brain tissue. The BBB protects the brain micro-environment from the outside environment, but at the same time, the BBB also stops most neuroprotective drugs from entering. Cerebrovascular blood volume accounts for only 3% of the brain volume, and in a cerebral ischemic stroke the local blood flow decreases or even stops. Therefore, the conventional oral or intravenous delivery methods may not be able to reach the lesion.

In addition, it is difficult for a CDPC molecule, which has a strong polarity, to permeate the BBB. Increasing the dosage can improve the CDPC concentration in brain tissue, but it may also increase adverse effects of the CDPC.

In 1994, Bobo developed the concept of drug delivery via brain extracellular space (ECS) for treating encephalopathy. His work focused on macromolecular drugs which are driven by pressure, then diffused in the ECS and distributed to the target region of the brain. Currently most of the neuroprotective drugs are small molecule compounds less than 1,000 daltons, which have no successful reports on treating stroke via ECS.

SUMMARY OF THE INVENTION

The technical problem to be solved by the present invention is to provide an administration method of CDPC (small molecules) for treating stroke. The method can decrease the concentration of CDPC entering the brain and further decrease the dosage while improving efficacy. Thus, the result is improved and the probability of adverse effects due to the drug is reduced.

Thus, the present invention provides an administration method for CDPC for treating stroke. CDPC was delivered via brain ECS at a concentration of 40 mmol/L-60 mmol/L.

In a specific embodiment of the present invention, the delivery concentration of CDPC is 50 mmol/L; or CDPC is administered at a flow rate of 0.2 μL/min at one time with a dose of 2 μL; or the administration site is in the caudate nucleus.

DETAILED DESCRIPTION OF THE EMBODIMENTS

The preferred embodiments of the present invention are described below with reference to the accompanying drawings.

Experimental conditions: Sprague Dawley rats weighing about 250-300 g with a brain tissue volume of 1.5 mL were used. The subjects were divided into eight groups, and each group had eight rats.

The administration process: seven groups of the rats, i.e., the ECS group, were administered CDPC via brain ECS and the last group, i.e., the IP group, were intraperitoneally injected with a concentration of 1000 mM CDPC. CDPC solution was injected via ECS in the caudate nucleus of the rats in the ECS groups with drug concentrations of 25 mM (mmol/L), 40 mM, 50 mM, 60 mM, 75 mM, 100 mM and 245 mM, respectively.

Efficacy validation: two hours after ECS administration and one hour after intraperitoneal injection, a permanent focal cerebral ischemia model was made by middle cerebral artery occlusion (MCAO). The brains of rats from each group were removed 12 hours after cerebral ischemia. The brain slices were obtained by cutting the brain at every 2 mm (5 slices from each rat). Then the slices were stained with 2,3,5-triphenyl-2H-tetrazolium chloride (TTC) for evaluating the cerebral infarction size and the effectiveness of administration of the drug via ECS.

Experiment 1: ECS Group

CDPC concentration: 25 mM
Flow rate: 0.2 μL/min
Injection volume: 2 μL, i.e., 1.33 μL/mL volume of brain tissue 2 hours after CDPC administration, permanent focal cerebral ischemia models of the rats were made by MCAO. Infarction percentages after 12 hours of cerebral ischemia in the rats are shown below:

| Rat No. | 84 | 86 | 94 | 97 | 98 | 99 | 103 | 104 |
|---|---|---|---|---|---|---|---|---|
| Infarction percentages % | 33.7 | 5.6 | 18.6 | 34.1 | 38.1 | 42 | 24.9 | 22.8 |

Mean Infarction percentage: 27.48
Standard deviation: 11.91

Figure 1:
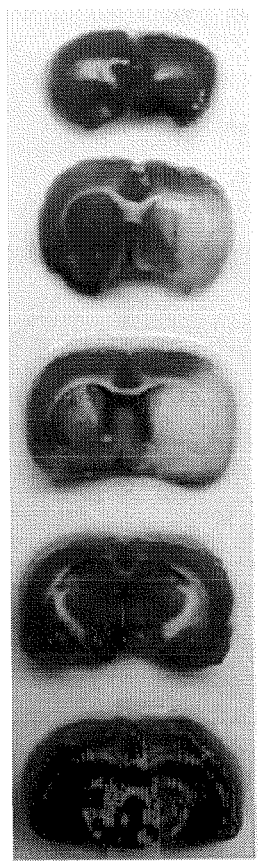
FIG. 1 shows TTC-stained rat brain slices after administration of CDPC via ECS at a concentration of 25 mM.

FIG. 1 shows the TTC-stained brain slices of rat No. 103 after 12 hours ischemia.

Experiment 2: ECS Group

CDPC concentration: 40 mM
Flow rate: 0.2 μL/min
Injection volume: 2 μL, i.e., 1.33 μL/mL volume of brain tissue 2 hours after CDPC administration, permanent focal cerebral ischemia models of the rats were made by MCAO. The infarction percentages after 12 hours of cerebral ischemia in the rats were:

| Rat No. | 284 | 286 | 294 | 297 | 298 | 299 | 303 | 304 |
|---|---|---|---|---|---|---|---|---|
| Infarction percentages % | 2.3 | 6.7 | 2.2 | 2.9 | 6.9 | 3.6 | 3.6 | 5.3 |

Mean infarction percentage: 4.18
Standard deviation: 1.88

Figure 2:
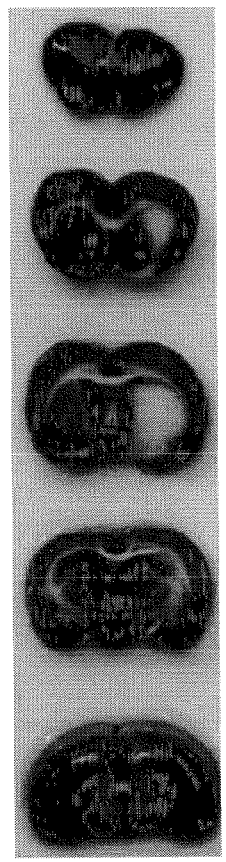
FIG. 2 shows TTC-stained rat brain slices after administration of CDPC via ECS at a concentration of 40 mM.

FIG. 2 shows the TTC-stained brain slices of rat No. 299 after 12 hours ischemia.

Experiment 3: ECS Group

CDPC concentration: 50 mM
Flow rate: 0.2 μL/min
Injection volume: 2 μL, i.e., 1.33 μL/mL volume of brain tissue 2 hours after CDPC administration, permanent focal cerebral ischemia models of the rats were made by MCAO. The infarction percentages after 12 hours of cerebral ischemia in the rats were:

| Rat No. | 15 | 19 | 20 | 21 | 29 | 45 | 49 | 57 |
|---|---|---|---|---|---|---|---|---|
| Infarction percentages % | 1.3 | 5.7 | 3 | 1.7 | 3.7 | 4.8 | 5 | 7.3 |

Mean infarction percentage: 4.06
Standard deviation: 2.04

Figure 3:
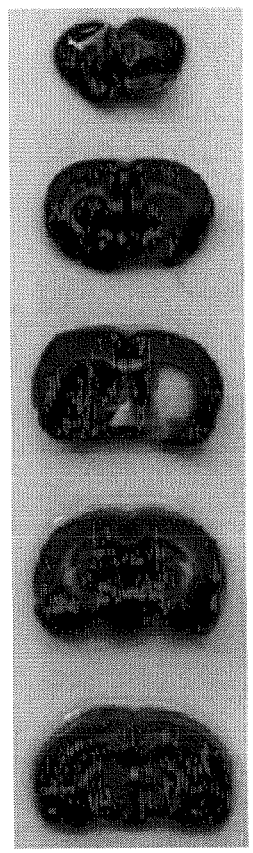
FIG. 3 shows TTC-stained rat brain slices after administration of CDPC via ECS at a concentration of 50 mM.

FIG. 3 shows the TTC-stained brain slices of rat No. 15 after 12 hours ischemia.

Experiment 4: ECS Group

CDPC concentration: 60 mM
Flow rate: 0.2 μL/min
Injection volume: 2 μL, i.e., 1.33 μL/mL volume of brain tissue 2 hours after CDPC administration, permanent focal cerebral ischemia models of the rats were made by MCAO. The infarction percentages after 12 hours of cerebral ischemia in the rats were:

| Rat No. | 313 | 314 | 315 | 318 | 319 | 320 | 321 | 322 |
|---|---|---|---|---|---|---|---|---|
| Infarction percentages % | 2.3 | 3.7 | 3.6 | 1.7 | 6.7 | 8.8 | 3.5 | 4.2 |

Mean infarction percentage: 4.32
Standard deviation: 2.32

Figure 4:
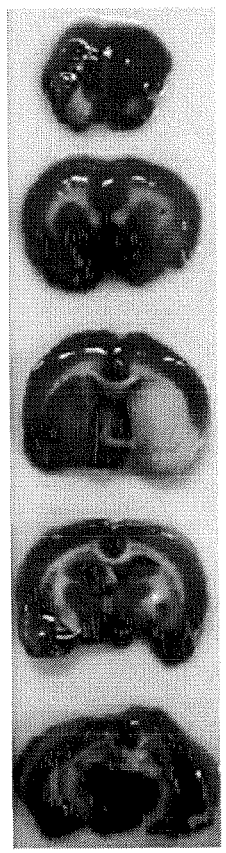
FIG. 4 shows TTC-stained rat brain slices after administration of CDPC via ECS at a concentration of 60 mM.

FIG. 4 shows the TTC-stained brain slices of rat No. 321 after 12 hours ischemia.

Experiment 5: ECS Group

CDPC concentration: 75 mM
Flow rate: 0.2 μL/min
Injection volume: 2 μL, i.e., 1.33 μL/mL volume of brain tissue 2 hours after CDPC administration, permanent focal cerebral ischemia models of the rats were made by MCAO. The infarction percentages after 12 hours of cerebral ischemia in the rats were:

| Rat No. | 113 | 114 | 115 | 118 | 119 | 120 | 121 |
|---|---|---|---|---|---|---|---|
| Infarction percentages % | 31.2 | 35.8 | 4.0 | 37.8 | 16.1 | 29.8 | 13.2 |

Mean infarction percentage: 24.0
Standard deviation: 12.87

Figure 5:
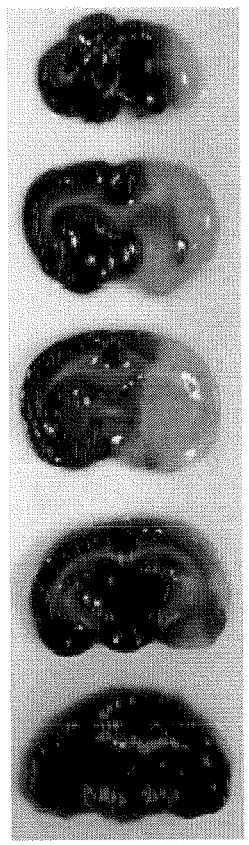
FIG. 5 shows TTC-stained rat brain slices after administration of CDPC via ECS at a concentration of 75 mM.

FIG. 5 shows the TTC-stained brain slices of rat No. 119 after 12 hours ischemia.

Experiment 6: ECS Group

CDPC concentration: 100 mM
Flow rate: 0.2 μL/min
Injection volume: 2 μL, 1.33 μL/mL volume of brain tissue 2 hours after CDPC administration, permanent focal cerebral ischemia models of the rats were made by MCAO. The infarction percentages after 12 hours of cerebral ischemia in the rats were:

| Rat No. | 88 | 91 | 93 | 96 | 100 | 109 | 111 | 112 |
|---|---|---|---|---|---|---|---|---|
| Infarction percentages % | 29.1 | 35.9 | 20.7 | 8.1 | 38.8 | 20.6 | 11.5 | 41.6 |

Mean infarction percentage: 23.53
Standard deviation: 11.67

Figure 6:
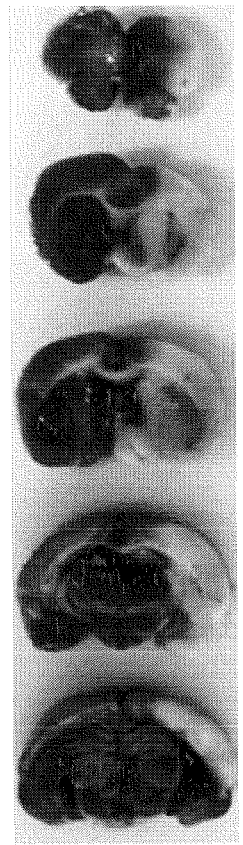
FIG. 6 shows TTC-stained rat brain slices after administration of CDPC via ECS at a concentration of 100 mM.

FIG. 6 shows the TTC-stained brain slices of rat No. 93 after 12 hours ischemia.

Experiment 7: ECS Group

CDPC concentration: 245 mM
Flow rate: 0.2 μL/min
Injection volume: 2 μL, i.e., 1.33 μL/mL volume of brain tissue 2 hours after CDPC administration, permanent focal cerebral ischemia models of the rats were made by MCAO. The infarction percentages after 12 hours of cerebral ischemia in the rats were:

| Rat No. | 51 | 52 | 56 | 58 | 75 | 76 | 77 | 79 |
|---|---|---|---|---|---|---|---|---|
| Infarction percentages % | 24.8 | 51.2 | 14.8 | 20 | 26.7 | 18.1 | 48.3 | 33.4 |

Mean infarction percentage: 29.66
Standard deviation: 12.77

Figure 7:
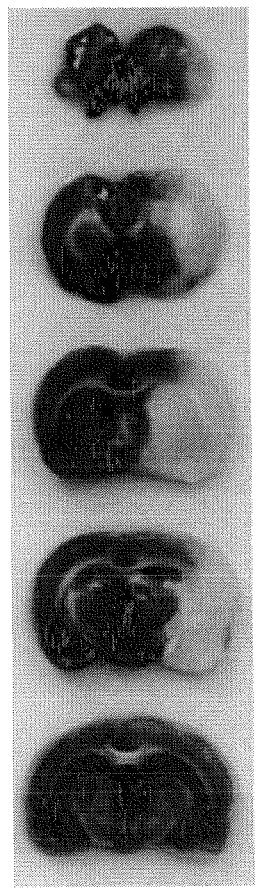
FIG. 7 shows TTC-stained rat brain slices after administration of CDPC via ECS at a concentration of 245 mM.

FIG. 7 shows the TTC-stained brain slices of rat No. 51 after 12 hours ischemia.

Experiment 8: IP Group

CDPC concentration of the infusion: 1000 mM
Flow rate: 1 mL/min
Injection volume: 1 mL, about 4 mL/kg weight 1 hour after CDPC administration, permanent focal cerebral ischemia models of the rats were made by MCAO. The infarction percentages after 12 hours of cerebral ischemia in the rats were:

| Rat No. | 35 | 38 | 39 | 40 | 41 | 42 | 53 | 54 |
|---|---|---|---|---|---|---|---|---|
| Infarction percentages % | 30.6 | 26.4 | 10.7 | 5.2 | 25.5 | 27.0 | 33.9 | 32.3 |

Mean infarction percentage: 24.0
Standard deviation: 10.4

Figure 8:
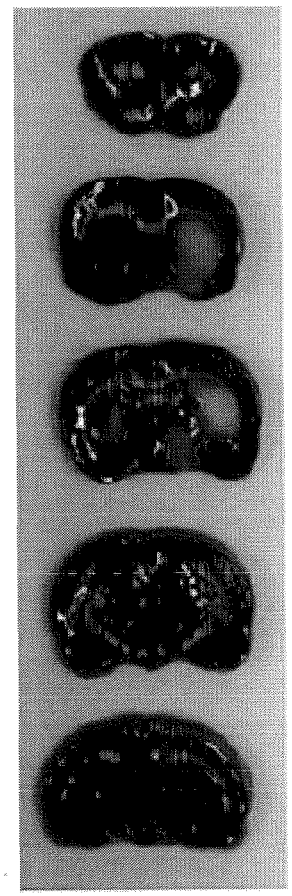
FIG. 8 shows TTC-stained rat brain slices after administration of CDPC via intraperitoneal injection at a concentration of 1000 mM.

FIG. 8 shows the TTC-stained brain slices of rat No. 39 after 12 hours ischemia.

Figure 9:
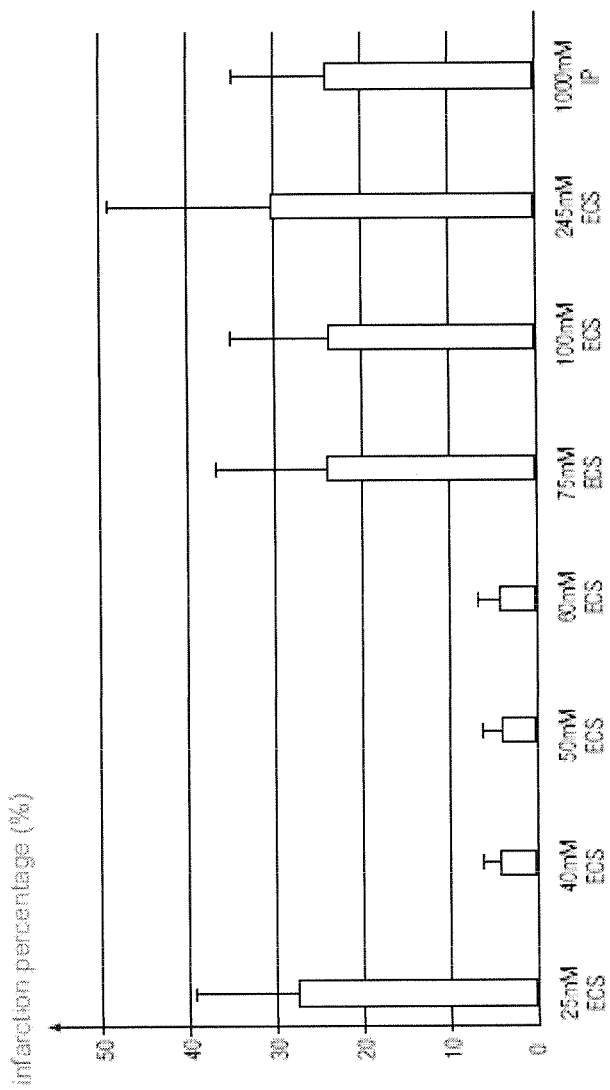
FIG. 9 shows a histogram of the mean volume percentages of experimental data of the above groups after correction.

FIG. 9 shows a histogram of the mean volume percentages of experimental data of the above groups after correction. As shown in FIG. 9, when administering CDPC via ECS at a flow rate of 0.2 μL/min, a volume of 2 μL and a concentration of 40-60 mM, there is a significant effect in treating the cerebral ischemia of rats.

The rat has mostly the same brain neurons and drug resistance as that of humans. CDPC delivery via ECS is also used for treating stroke in humans. Therefore, a suitable concentration in the human brain is 40 mM to 60 mM, in which 50 mM works best. CDPC dosage delivery via ECS is significantly lower than via oral delivery (with a dosage of 0.5-2 g daily for humans), intravenous delivery (1 g daily was reported better than 0.25 g daily for humans) and intraperitoneal delivery (0.1-0.5 g/kg daily for rats). Therefore, treating results of stroke are guaranteed and the side effects, such as intracranial bleeding caused by CDPC, are reduced.

Assuming the volume of a 250-300 g Sprague Dawley rat's brain is A and the volume of a healthy adult human brain is B, if the CDPC dosage via ECS for rat brain is known, we can gain the CDPC dosage for human brain via ECS approach according to the proportion of ECS volume (the volume of interstitial fluid in the brain tissue) to that of rat brain and human brain.

The formula is:

$$\text{CDPC dosage for human brain} = (B \times \alpha_M \times \text{CDPC dosage for rat brain})/(A \times \alpha_R)$$

Wherein:
$\alpha_R$ is the volume ratio of ECS to brain for a rat, which was measured to be 0.21;
$\alpha_M$ is the volume ratio of ECS to brain for human, which was measured to be 0.24;
A is rat brain volume, which was 1.5 ml of a 250-300 grams Sprague Dawley rat brain;
B is human brain volume, which was 1278 mL of the normal adult (Qingshi Zeng, "Quantitative Analysis of MIR of adult brains with different ages", in Acta Academiae Medicinae Sinicae Vol 128, pp. 795-798).

In the above formula: $A \times \alpha_R$ is the volume of ECS for a rat brain; $B \times \alpha_M$ is the volume of ECS for human brain. If the dose for a rat brain is 2 μL, the dose for a human brain is calculated to be 1947 μL (approximately 2 ml).

What is claimed is:

1. A method for administration of citicoline (CDPC) in stroke treatment, wherein a CDPC solution is administered to a subject in need thereof via brain extracellular space (ECS) at a concentration of 40 mmol/L-60 mmol/L, wherein the CDPC solution is administered to the subject in the caudate nucleus.

2. The method according to claim 1, wherein the concentration of CDPC in solution is 50 mmol/L.

3. The method according to claim 2, wherein the CDPC solution is administered at a flow rate of 0.2 μL/min and a dose of 1.33 μL/mL volume of brain tissue.

4. The method according to claim 1, wherein the concentration of CDPC in solution is 40 mmol/L.

5. The method according to claim 4, wherein the CDPC solution is administered at a flow rate of 0.2 μL/min and a dose of 1.33 μL/mL volume of brain tissue.

6. The method according to claim 1, wherein the concentration of CDPC in solution is 60 mmol/L.

7. The method according to claim 6, wherein the CDPC solution is administered at a flow rate of 0.2 μL/min and a dose of 1.33 μL/mL volume of brain tissue.

8. The method according to claim 1, wherein the CDPC solution is administered once to the subject at a flow rate of 0.2 μL/min and a dose of 1.33 μL/mL volume of brain tissue.

9. The method according to claim 1, wherein the CDPC solution is administered more than once to the subject at a flow rate of 0.2 μL/min and a dose of 1.33 μL/mL volume of brain tissue.

10. A method for the treatment of stroke, wherein a CDPC solution is administered to a subject in need thereof via brain ECS at a concentration of 40 mmol/L-60 mmol/L, wherein the CDPC solution is administered to the subject in the caudate nucleus, wherein the size of a cerebral infarction following cerebral ischemia in the subject is less than 20% after administration of the CDPC to the subject.

11. The method according to claim 10, wherein the size of a cerebral infarction following cerebral ischemia in the subject is less than 10% after administration of the CDPC to the subject.

12. The method according to claim 11, wherein the size of a cerebral infarction following cerebral ischemia in the subject is less than 7% after administration of the CDPC to the subject.

13. The method according to claim 12, wherein the size of a cerebral infarction following cerebral ischemia in the subject is less than 5% after administration of the CDPC to the subject.

14. The method of claim 10, wherein the concentration of CDPC in solution is about 50 mmol/L.

15. The method of claim 10, wherein the CDPC solution is administered at a flow rate of 0.2 μL/min and a dose of 1.33 μL/mL volume of brain tissue.

16. The method of claim 10, wherein the size of a cerebral infarction following cerebral ischemia in the subject is less than 20% 12-16 hours after administration of the CDPC to the subject.

* * * * *